US005738612A

United States Patent [19]
Tsuda

[11] Patent Number: 5,738,612
[45] Date of Patent: Apr. 14, 1998

[54] EXERCISE APPARATUS HAVING EXERCISE-LOAD CHANGING FUNCTION

[75] Inventor: Hideichi Tsuda, Komaki, Japan

[73] Assignee: Colin Corporation, Komaki, Japan

[21] Appl. No.: 760,600

[22] Filed: Dec. 4, 1996

[51] Int. Cl.$^6$ ................................................. A63B 21/00
[52] U.S. Cl. ...................... 482/8; 482/5; 482/9; 482/57; 482/900; 128/707
[58] Field of Search .................... 128/707, 630, 128/668, 680, 695 R, 696, 700, 718; 482/1–8, 9, 51, 52, 54, 57, 70–72, 900–902

[56] References Cited

U.S. PATENT DOCUMENTS

| | | |
|---|---|---|
| 3,675,640 | 7/1972 | Gatts . |
| 4,408,614 | 10/1983 | Weaver et al. . |
| 5,170,796 | 12/1992 | Kobayashi . |
| 5,318,487 | 6/1994 | Golen et al. ................................. 482/8 |
| 5,462,504 | 10/1995 | Trulaske et al. ............................. 482/8 |
| 5,527,239 | 6/1996 | Abbondanza ................................ 482/8 |

FOREIGN PATENT DOCUMENTS

0 028 209 A1  5/1981  European Pat. Off. .

Primary Examiner—Richard J. Apley
Assistant Examiner—Glenn E. Richman
Attorney, Agent, or Firm—Oliff & Berridge, PLC

[57] ABSTRACT

An exercise apparatus including an exercise-load applying device which applies an exercise load to a person such as a patient, an exercise-load changing device which changes the exercise load applied to the person by the exercise-load applying device, a pulse-rate measuring device which successively measures a pulse rate of the person in synchronism with a heartbeat of the person, a blood-pressure measuring device which successively and non-invasively measures a blood pressure of the person in synchronism with the heartbeat of the person, a calculating device which successively calculates a product of the pulse rate and the blood pressure in synchronism with the heartbeat of the person, and a control device which controls the exercise-load changing device to change the exercise load applied to the person by the exercise-load applying device, so that the products successively calculated by the calculating device substantially coincide with a predetermined target value.

9 Claims, 7 Drawing Sheets

EXERCISE APPARATUS HAVING EXERCISE-LOAD CHANGING FUNCTION

BACKGROUND OF THE INVENTION

1. Field of the Invention

The present invention relates to an exercise apparatus having the function of changing an exercise load applied to a person who is doing exercise thereon.

2. Related Art Statement

There is known an exercise apparatus which applies an exercise load to a person who is doing exercise thereon for measuring the ability of his or her motile organ, or training his or her body. For example, an ergometer or a treadmill is known as the exercise apparatus. The ergometer includes a pair of pedals which are rotated by a pair of feet of a person, respectively. The treadmill includes an endless belt which is movable or turnable while supporting a person who is walking or running thereon. U.S. Pat. No. 3,675,640 discloses an exercise apparatus which can be provided with a reference value used for identifying an excessively high exercise load being applied to a person. The reference value may be a pulse rate or a blood pressure higher by a predetermined ratio than person's actual rate or pressure measured while he or she is at rest before an exercise test is started. When person's actual rate or pressure exceeds the reference value during the exercise test, the exercise apparatus issues an alarm sound or automatically reduces the exercise load being applied to his or her body.

Thus, in the above-identified prior art, an actual pulse rate or blood pressure of a person is utilized for setting a reference value used for identifying an excessive exercise load applied to the person. However, pulse rate or blood pressure cannot accurately indicate "internal" load applied to person's body. Therefore, the prior exercise apparatus may apply an excessively high or low load to a person such as a patient or a trainee. In particular, in the case where an exercise test is carried out, without a medical specialist, on a person who has a low cardiac function, such as an old person or a person having a circulatory disease, if the prior apparatus applies an excessively high load to the person, he or she may suffer heart attack due to the excessive exercise load. Meanwhile, in the case where only an excessively low load is applied to a trainee, his or her body cannot be well trained.

In the above-identified situation, the Assignee of the present application had proposed another exercise apparatus which iteratively calculates an actual pressure-rate product as the product of a blood pressure and a pulse rate of a person who is doing exercise thereon and which controls an exercise load applied to the person so that the calculated pressure-rate products may coincide with a predetermined target value. The second prior apparatus is disclosed in Japanese Patent Application laid open for opposition purposes under Publication No. 7-47053. Since pressure-rate product that is obtained as the product of a blood pressure and a pulse rate of a person who is doing exercise, accurately indicates internal load applied to the person, the second exercise apparatus can apply an appropriate exercise load to the person, while preventing an excessively high load, or while providing a good effect in training his or her body.

However, the above-identified second exercise apparatus includes a blood-pressure measuring device which determines a blood pressure of a person based on the variation of a plurality of heartbeat-synchronous pulses of a pulse wave obtained while the pressing pressure of a cuff is slowly changed. Accordingly, the second apparatus cannot measure a blood pressure of a person at a cyclic period shorter than several tens of seconds, therefore, cannot calculate a pressure-rate product at a period shorter than several tens of seconds. Thus, the second apparatus may delay adjusting the exercise load applied to the person. That is, even the second exercise apparatus may not apply an appropriate exercise load to a person who is doing exercise thereon.

SUMMARY OF THE INVENTION

It is therefore an object of the present invention to provide an exercise apparatus which successively calculates a pressure-rate product at a short period and continues to apply an appropriate exercise load to a person who is doing exercise thereon.

The above object has been achieved by the present invention, which provides an exercise apparatus comprising an exercise-load applying device which applies an exercise load to a person; an exercise-load changing device which changes the exercise load applied to the person by the exercise-load applying device; a pulse-rate measuring device which successively measures a pulse rate of the person in synchronism with a heartbeat of the person; a blood-pressure measuring device which successively and non-invasively measures a blood pressure of the person in synchronism with the heartbeat of the person; a calculating device which successively calculates a product of the pulse rate and the blood pressure in synchronism with the heartbeat of the person; and a control device which controls the exercise-load changing device to change the exercise load applied to the person by the exercise-load applying device, so that the products successively calculated by the calculating device substantially coincide with a predetermined target value.

In the exercise apparatus constructed as described above, the control device controls the exercise-load changing device to change the exercise load applied to the person by the exercise-load applying device, so that the pressure-rate products successively calculated by the calculating device substantially coincide with a predetermined target value. Since the pressure-rate products accurately indicate the internal load applied to the person, the present exercise apparatus can apply an appropriate exercise load to the person, depending upon the current blood pressure and pulse rate of the person who is doing exercise thereon. In particular, the present exercise apparatus effectively prevents an excessively high exercise load from being applied to a person who is in bad shape or has a low cardiac function, thereby avoiding the person from suffering, e.g., heart attack. In addition, the present exercise apparatus effectively trains a trainee. Moreover, the blood-pressure (BP) measuring device successively and non-invasively measures the BP values of the person in synchronism with the heartbeat of the person, and accordingly the calculating device successively calculates the pressure-rate products in synchronism with the heartbeat of the patient. Thus, the control device can appropriately adjust, without delay, the exercise load applied to the person so that the current pressure-rate product substantially coincides with the target value. Thus, the present exercise apparatus continues to apply an appropriate exercise load to the person.

In a preferred embodiment of the present invention, the blood-pressure measuring device comprises a pressing device which provides a pressing force to press a body portion of the person, a pressing-force changing device which changes the pressing force of the pressing device, standard-blood-pressure determining means for determining a standard blood pressure of the person based on a heartbeat-synchronous wave obtained while the pressing force of the pressing device is changed by the pressing-force changing device, a pressure-pulse-wave sensor adapted to be pressed against an artery of the person via a skin tissue above the artery so as to detect a magnitude of a pressure pulse wave produced from the artery in synchronism with the heartbeat of the person, relationship determining means for determining a relationship between blood pressure and magnitude of pressure pulse wave, based on the standard blood pressure determined by the standard-blood-pressure determining means and the magnitude of the pressure pulse wave detected by the pressure pulse wave sensor, and blood-pressure estimating means for successively estimating a blood pressure of the person, based on a magnitude of each of a plurality of heartbeat-synchronous pulses of the pressure pulse wave detected by the pressure pulse wave sensor, according to the relationship determined by the relationship determining means. A standard BP value determined by the standard-BP determining means is highly reliable, and a relationship between BP value and magnitude of pressure pulse wave is determined based on the highly reliable standard BP value and a magnitude of a pressure pulse wave detected by the pressure pulse wave sensor. The BP estimating means successively estimates a BP value of the person, based on a magnitude of each of a plurality of heartbeat-synchronous pulses of an actual pressure pulse wave detected by the pressure pulse wave sensor, according to the thus determined relationship between BP value and magnitude of pressure pulse wave. Thus, the estimated BP values, successively obtained in synchronism with the heartbeat of the person, enjoy a considerably high accuracy.

In another embodiment of the present invention, the pressing device comprises an inflatable cuff adapted to be wound around the body portion of the person, the pressing-force changing device comprising a cuff-pressure changing device which changes a fluid pressure in the cuff, the standard-blood-pressure determining means comprising means for determining the standard blood pressure of the person based on a variation of respective amplitudes of a plurality of heartbeat-synchronous pulses of the heartbeat-synchronous wave which is a pressure oscillation produced in the cuff while the pressure of the cuff is changed by the cuff-pressure changing device.

In another embodiment of the present invention, the pressing device comprises an inflatable cuff adapted to be wound around the body portion of the person, the pressing-force changing device comprising a cuff-pressure changing device which changes a fluid pressure in the cuff, the standard-blood-pressure determining means comprising means for determining the standard blood pressure of the person based on a fluid pressure of the cuff at a time when a Korotkoff sound is first detected, or last detected, from the body portion while the pressure of the cuff is changed by the cuff-pressure changing device.

In another embodiment of the present invention, the pressure pulse wave sensor comprises a flat surface adapted to be pressed against the artery of the person via the skin tissue, a plurality of pressure sensing elements arranged in the flat surface, and a flat-surface pressing device which presses the flat surface against the artery via the skin tissue, and the blood-pressure measuring device comprises means for controlling the flat-surface pressing device to press the flat surface against the artery via the skin tissue such that a portion of a wall of the artery is flattened under the flat surface. In this case, since a portion of the wall of the artery is flattened under the flat surface in which the plurality of pressure sensing elements are provided, the pressure pulse wave (PPW) detected by each of the pressure sensing elements is least influenced by the tensile force of the arterial wall. Thus, the detected PPW enjoys a high accuracy and accordingly the BP-PPW relationship determined based on the detected PPW enjoys a high accuracy. In addition, the estimated BP values and the calculated pressure-rate products also enjoy a high accuracy.

In another embodiment of the present invention, the standard-blood-pressure determining means comprises means for determining the standard blood pressure of the person, before the control device begins controlling the exercise-load changing device to change the exercise load applied to the person by the exercise-load applying device so that the products successively calculated by the calculating device substantially coincide with the predetermined target value, and the relationship determining means comprises means for determining the relationship between blood pressure and magnitude of pressure pulse wave, based on the standard blood pressure determined by the standard-blood-pressure determining means and the magnitude of the pressure pulse wave detected by the pressure pulse wave sensor before the control device begins controlling the exercise-load changing device. In the case where the BP-PPW relationship is determined just before the commencement of the exercise-load control operation of the control device, estimated BP values are provided with higher accuracy according to the new BP-PPW relationship and accordingly pressure-rate products are calculated with higher accuracy.

In another embodiment of the present invention, the exercise apparatus further comprises abnormality identifying means for identifying an abnormality of the person when one of the pulse rates successively measured by the pulse-rate measuring device is greater than a reference value, and the control device controls, when the abnormality identifying means identifies the abnormality, the exercise-load changing device to decrease the exercise load applied to the person by the exercise-load applying device. Even when an abnormality occurs to the person, the present exercise apparatus can effectively prevent an excessively high exercise load from being applied to the person.

In another embodiment of the present invention, the exercise-load applying device comprises a pair of pedals adapted to be rotated by a pair of feet of the person, respectively, and a rotary member which is rotatable with the pedals, and the exercise-load changing device comprises means for changing a resistance to the rotation of the rotary member with the pedals. The resistance applied to the rotary member may be changed either mechanically or electromagnetically.

In another embodiment of the present invention, the exercise-load applying device comprises an endless belt which is movable while supporting the person who is moving thereon, and the exercise-load changing device comprises means for changing a speed of movement of the endless belt. The person may walk or run on the endless belt which may be turned by an electric motor. In the last case, the exercise-load changing device may comprise means for changing the electric power supplied to the electric motor.

BRIEF DESCRIPTION OF THE DRAWINGS

The above and optional objects, features, and advantages of the present invention will better be understood by reading the following detailed description of FIG. 1 is a diagrammatic view of an exercise apparatus having an exercise-load changing function to which the present invention is applied.

DETAILED DESCRIPTION OF THE PREFERRED EMBODIMENTS

Referring to FIGS. 1 to 6, there will be described an exercise apparatus 4 having an exercise-load changing function to which the present invention is applied. The exercise apparatus 4 includes an ergometer 6 having a pair of pedals 65 which are rotated by a pair of feet of a person such as a patient, and a blood-pressure (BP) measuring device 8 which successively measures a BP value of the person in synchronism with the heartbeat of the person.

Figure 1:
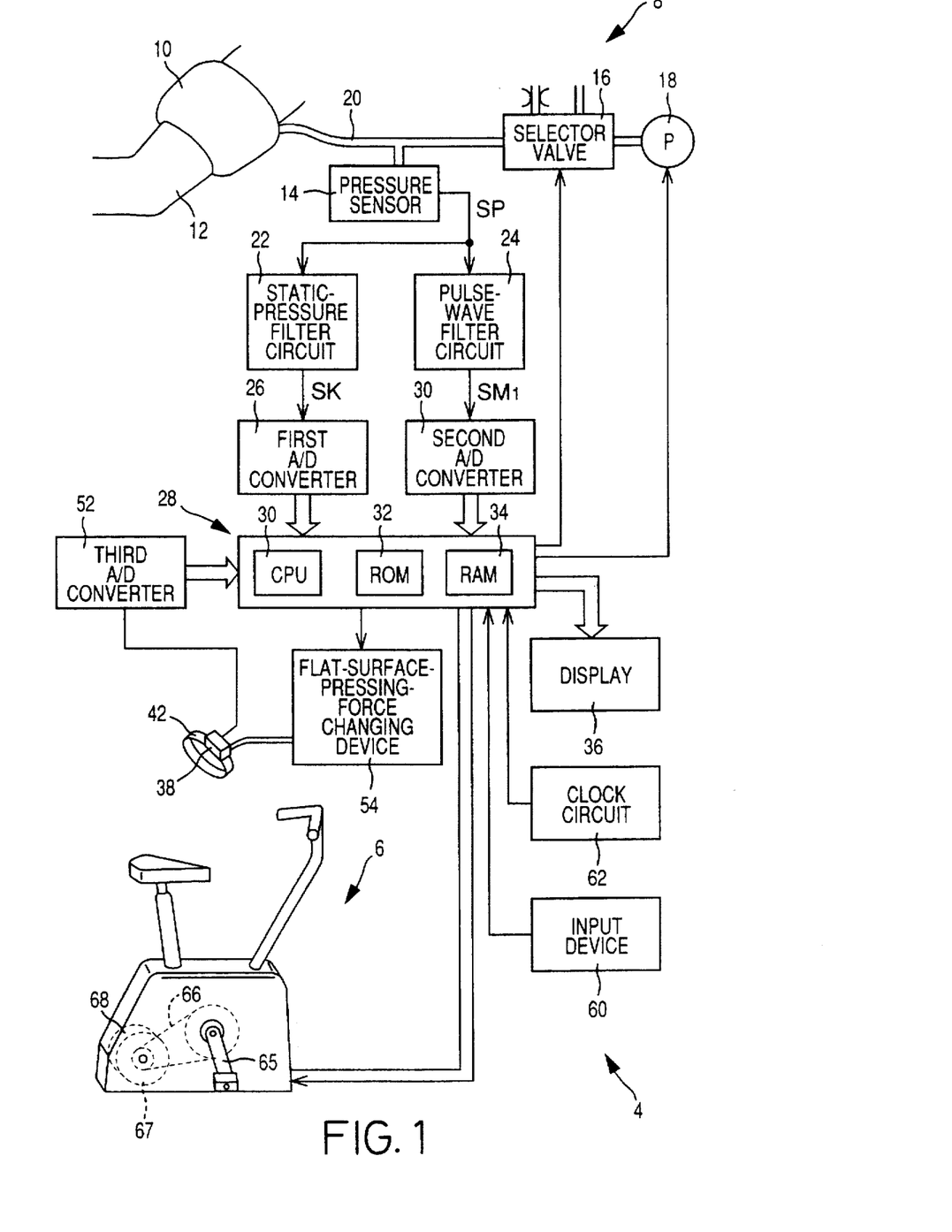

In FIG. 1, the BP measuring device 8 includes an inflatable cuff 10 having a rubber bag and a band-like cloth bag in which the rubber bag is accommodated. The cuff 10 is wound around, e.g., an upper arm 12 of a patient. The cuff 10 is connected via piping 20 to a pressure sensor 14, a selector valve 16, and a first air pump 18. The selector valve 16 is selectively placed, under control of an electronic control device 28, in a first state in which the valve 16 permits pressurized air to be supplied from the air pump 18 to the cuff 10 to increase the pressure of the cuff 10 (hereinafter, referred to as the "cuff pressure"), a second state in which the valve 16 causes the cuff 10 to be deflated slowly, and a third state in which the valve 16 causes the cuff 10 to be deflated quickly.

The pressure sensor 14 detects the cuff pressure (i.e., pressure in the cuff 10), and generates a pressure signal, SP, representing the detected cuff pressure. The pressure signal SP is supplied to each of a static-pressure filter circuit 22 and a pulse-wave filter circuit 24. The static-pressure filter circuit 22 includes a low-pass filter which extracts, from the pressure signal SP, a cuff-pressure signal, SK, representing a static or direct-current component of the pressure signal SP. The cuff-pressure signal SK is supplied via a first analog-to-digital (A/D) converter 26 to the control device 28.

The pulse-wave filter circuit 24 includes a band-pass filter which extracts, from the pressure signal SP, a pulse-wave signal, $SM_1$, representing an oscillating or alternating-current component of the pressure signal SP, based on a frequency characteristic of the signal $SM_1$. The pulse-wave signal $SM_1$ is supplied via a second A/D converter 30 to the control device 28. The oscillating or alternating-current component represented by the pulse-wave signal $SM_1$ corresponds to an oscillatory pressure wave, i.e., pulse wave which is produced from a brachial artery (not shown) of patient's upper arm 12 in synchronism with the heartbeat of the patient and is propagated via skin tissue to the cuff 10. This pulse wave is referred to as the "cuff pulse wave (CPW)" to be distinguished from a "pressure pulse wave (PPW)" which will be explained later. In the present embodiment, the cuff 10, the pressure sensor 14, and the pulse-wave filter circuit 24 cooperate with one another to provide a cuff pulse wave (CPW) sensor.

The control device 28 is provided by a microcomputer including a central processing unit (CPU) 30, a read only memory (ROM) 32, a random access memory (RAM) 34, and an input and output (I/O) port (not shown). The CPU 30 processes input signals, including the signals SK, $SM_1$, by utilizing the temporary-storage function of the RAM 34, according to the control programs pre-stored in the ROM 32. In addition, the CPU 30 supplies drive signals via the I/O port to drive circuits (not shown) which are provided for the selector valve 16 and the air pump 18, respectively. Thus, the CPU 30 controls respective operations of the valve 16 and the pump 18. For example, when an oscillometric BP measurement using the cuff 10 is carried out to calibrate the BP measuring device 8, the CPU 30 controls the valve 16 and the pump 18 to increase quickly the cuff pressure up to a predetermined target value and subsequently decrease the cuff pressure at a low rate of 2 to 3 mmHg/sec. Based on the variation of the cuff pulse wave (CPW) represented by the pulse-wave signal $SM_1$ provided by the pulse-wave filter circuit 24 during the low-rate decreasing of the cuff pressure, the CPU 30 determines a systolic and a diastolic BP value of the patient, according to a known oscillometric BP measuring method. In addition, the CPU 30 controls a display device 36 to display the thus determined BP values.

Figure 2:
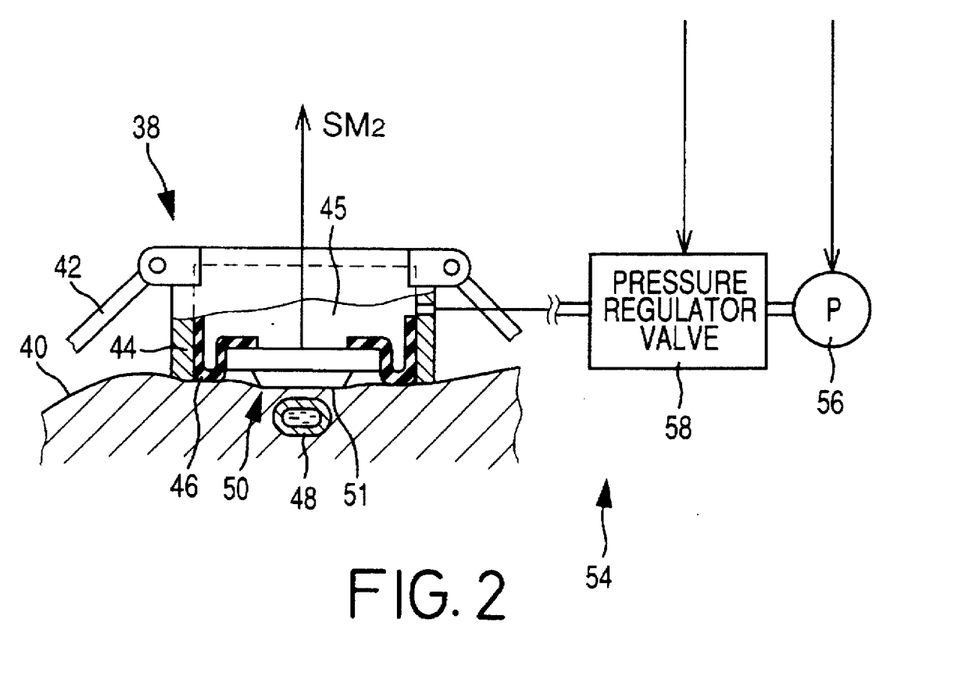
FIG. 2 is a view of a pressure pulse wave (PPW) sensor having a flat surface, and a flat-surface-pressing-force changing device, of the exercise apparatus of FIG. 1.

As shown in FIG. 2, a pressure-pulse-wave (PPW) sensor 38 includes a container-like sensor housing 44, and a pair of fastening bands 42 connected to the sensor housing 44. With the help of the fastening bands 42, the PPW sensor 38 is detachably attached to a wrist of the same arm 12 of the patient on which the cuff 10 is worn, or the other arm of the patient, such that an opening of the sensor housing 44 is opposed to a body surface or skin 40 of the patient. A press member 50 is secured via an elastic diaphragm 46 to inner surfaces of the sensor housing 44 such that the press member 50 is movable relative to the housing 44 and is advanceable through the opening of the housing 44 toward the body surface 40 of the patient. The sensor housing 44 and the diaphragm 46 cooperate with each other to define a pressure chamber 45, which is supplied with pressurized air from a second air pump 56 via a pressure regulator valve 58. Thus, the press member 50 is pressed on the body surface 40, that is, against a radial artery 48 with a pressing force, $P_{HD}$, corresponding to the air pressure in the pressure chamber 45. In the present embodiment, the pressing forces applied to the press member 50, i.e., applied to the body surface 40 are indicated in terms of pressure values (mmHg) in the pressure chamber 45. The sensor housing 44, the diaphragm 46, the pressure chamber 45, etc. cooperate with one another to provide a flat-surface pressing device which presses a flat surface 51 of the press member 50 against the radial artery 48 via the body surface or skin tissue 40. The second air pump 56 and the pressure regulator valve 58 cooperate with each other to provide a flat-surface-pressing-force changing device 54.

The press member 50 includes a semiconductor chip formed of a monocrystalline silicon with the flat surface 51, and a number of pressure-sensing semiconductor elements (not shown) which are arranged, in the flat surface 51, in an array at a regular interval of distance (about 0.2 mm), such that the array of pressure-sensing elements extends in the direction of width of the radial artery 48. When the press member 50 is pressed against the radial artery 48 via the body surface 40, each sensor element detects an oscillatory pressure wave, i.e., pressure pulse wave (PPW) which is produced from the radial artery 48 in synchronism with the heartbeat of the patient and is propagated via the body surface 40 to the press member 50. The PPW sensor 38 generates a PPW signal, $SM_2$, representing the detected PPW, and supplies the PPW signal $SM_2$ to the control device 28 via a third A/D converter 52.

The CPU 30 of the control device 28 processes the input signals, including the PPW signal $SM_2$, by utilizing the temporary-storage function of the RAM 34, according to the control programs pre-stored in the ROM 32, and supplies drive signals to drive circuits (not shown) which are provided for the second air pump 56 and the pressure regulator valve 58, respectively. Thus, the CPU 30 controls respective operations of the pump 56 and the valve 58 and thereby regulates the pressure of the pressure chamber 45 that is applied to the press member 50, i.e., the pressing force of the press member 50 applied to the radial artery 48 via the body surface or skin tissue 40.

The present exercise apparatus 4 further includes an input device 60, such as a keyboard, through which an operator such as a doctor or a nurse inputs a predetermined target pressure-rate product, $PRP_M$, (described later), a predetermined coefficient used for identifying an abnormality of the patient (described later), etc. The thus input data are supplied to the control device 28. A clock circuit 62, connected to the control device 28, supplies a time of day to the control device 28 so that the control device 28 determines a time of day when a BP value is measured by the BP measuring device 8, or when a PPW is detected by the PPW sensor 38.

The ergometer 6 functions as an exercise-load applying device which applies an exercise load to the patient who undergoes an exercise test thereon. The ergometer 6 includes a pair of pedals 65, a chain 66, a rotary plate 67 which is operatively connected to the pedals 65 via the chain 66, and an electromagnetic brake 68 which applies a controllable resistance to the rotation of the rotary member 67. The brake 68 may be an eddy-current brake which can adjust the resistance applied to the rotation of the rotary plate 67, by changing the magnitude of an eddy current generated in the rotary plate 67. Otherwise, the brake 68 may be one which can adjust the resistance by changing the magnitude of an electric current induced in a revolving coil which is rotated with the rotary plate 67. The brake 68 functions as an exercise-load changing device which changes the exercise load which is applied by the ergometer 6 to the patient who is doing exercise thereon.

When an exercise test is started on a patient, the CPU 30 determines an optimum pressing force, $P_{HDP}$, of the PPW sensor 38 applied to the radial artery 48, based on the PPW (i.e., PPW signal $SM_2$) obtained while the pressure of the pressure chamber 45 is slowly changed, and controls the pressure regulator valve 58 to maintain the pressure of the chamber 45 at the determined optimum pressing force $P_{HDP}$. In addition, the CPU 30 determines a relationship between BP values and PPW magnitudes $P_M$ (i.e., absolute voltage values of the PPW signal $SM_2$), based on systolic and diastolic BP values, $BP_{SYS}$, $BP_{DIA}$, measured using the cuff 10 according a known oscillometric BP measuring method, and a maximum and a minimum magnitude, $P_{Mmax}$, $P_{Mmin}$, of one heartbeat-synchronous pulse of the PPW detected by the PPW sensor 38 being pressed on the body surface 40 with the optimum pressing force $P_{HDP}$. According to the thus determined relationship, the CPU 30 estimates a systolic and a diastolic BP value (i.e., estimated BP values), $MBP_{SYS}$, $MBP_{DIA}$, of the patient, based on a maximum magnitude (i.e., upper-peak magnitude) $P_{Mmax}$ and a minimum magnitude (i.e., lower-peak magnitude) $P_{Mmin}$ of each of successive heartbeat-synchronous pulses of the PPW detected by the PPW sensor 38 being pressed on the body surface 40 with the optimum pressing force $P_{HDP}$. Subsequently, the CPU 30 controls the display 36 to successively display, for each heartbeat-synchronous pulse, the estimated BP values $MBP_{SYS}$, $MBP_{DIA}$, in digits, and continuously display the waveform of the PPW detected by the PPW sensor 38. This waveform represents the instantaneous estimated BP values MBP of the patient.

Figure 4:
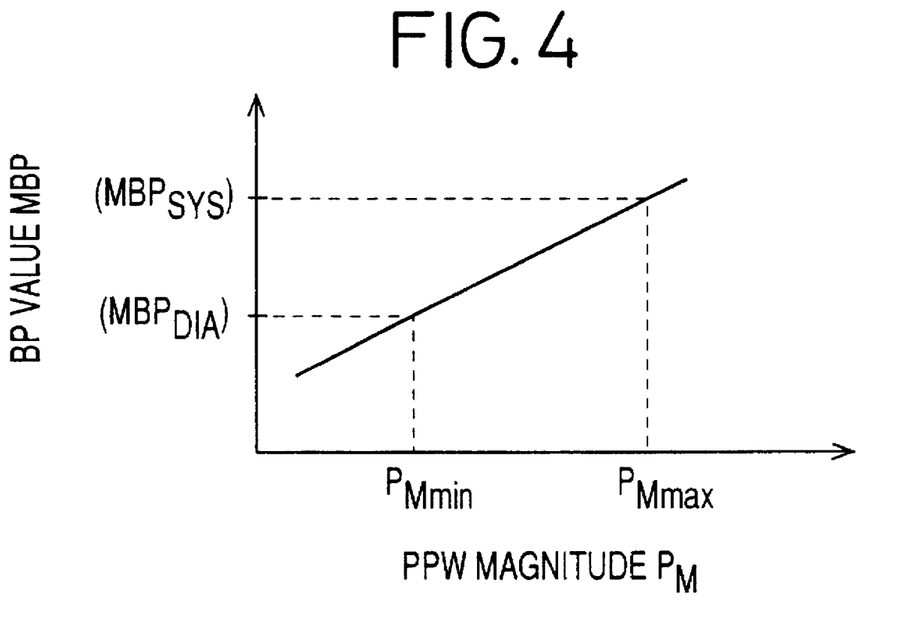
FIG. 4 is a graph showing a relationship between blood pressure and magnitude of pressure pulse wave determined by the control device of the apparatus of FIG. 1.

FIG. 4 shows an example of a relationship between BP values (estimated BP values MBP) and PPW magnitudes $P_M$ that is determined by the CPU 30. This relationship is expressed by the following linear function (1):

$$MBP = \alpha \cdot P_M + \beta \qquad (1)$$

where $\alpha$ is a constant corresponding to the slope of the linear function (1) and $\beta$ is a constant corresponding to the intercept of the axis of ordinate indicative of estimated BP values MBP.

Figure 3:
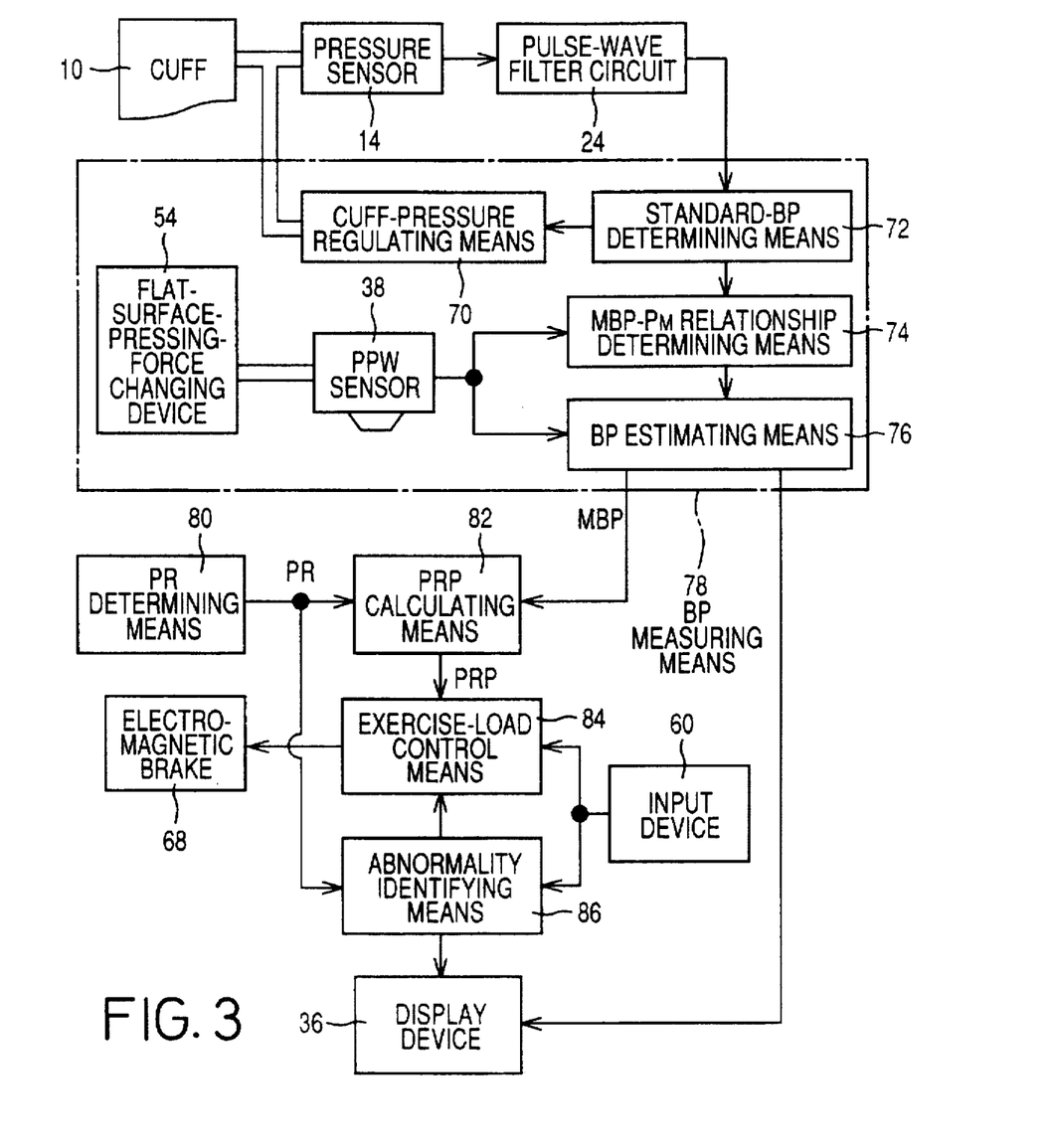
FIG. 3 is a block diagram for explaining various functions of a control device of the apparatus of FIG. 1.

FIG. 3 illustrates various functions of the control device 28 of the present exercise apparatus 4. The static-pressure filter circuit 22 cooperates with the control device 28 to provide a standard-BP determining means 72 which determines, according to an oscillometric BP measuring method (e.g., JIS T 1115; JIS is Japanese Industrial Standard), a systolic BP value $BP_{SYS}$, a mean BP value $BP_{MEAN}$, and a diastolic BP value $BP_{DIA}$ of a person based on the variation of respective amplitudes of heartbeat-synchronous pulses of the cuff pulse wave obtained while the pressure of the cuff 10 is slowly increased or decreased at the rate of 2 to 3 mmHg/sec. The cuff pulse wave (CPW) is represented by the pulse-wave signal $SM_1$ provided by the pulse-wave filter circuit 24. The thus determined BP values are standard BP values to be used for determining a MBP-$P_M$ relationship as shown in FIG. 4. The standard BP values are determined just before an exercise-load control means 84 (described below) starts controlling the electromagnetic brake 68 as the exercise-load changing device, and are displayed on the display device 36.

The PPW sensor 38 is preferably worn on the wrist of the other arm of the patient than the arm 12 on which the cuff 10 is worn, and detects the PPW produced from the radial artery 48 of the other arm. The flat-surface-pressing-force changing device 54 changes the pressing force of the flat-surface pressing device 44, 45, 46 applied to the flat surface 51 of the press member 50, so that a portion of the wall of the radial artery 48 is flattened under the flat surface 51 being pressed by the pressing device 44, 45, 46.

The control device 28 functions as a relationship determining means 74 which determines a MBP-$P_M$ relationship between estimated BP values MBP and PPW magnitudes $P_M$ that is expressed by the linear function (1) and is shown in FIG. 4, based on the magnitudes of PPW detected by the PPW sensor 38 and the standard BP values (at least two of the systolic, mean, and diastolic BP values $BP_{SYS}$, $BP_{MEAN}$, $BP_{DIA}$) determined by the standard-BP determining means 72.

The control device 28 also functions as a BP estimating means 76 which successively estimates, according to the MBP-$P_M$ relationship, a BP value MBP of the person based on a magnitude of each of heartbeat-synchronous pulses of the PPW detected by the PPW sensor 38. The estimated BP values MBP are successively displayed on the display device 36. The estimated BP values MBP may comprise an estimated systolic BP value corresponding to the maximum magnitude (i.e., upper-peak magnitude) of each heartbeat-synchronous pulse of the PPW signal $SM_2$, an estimated diastolic BP value corresponding to the minimum magnitude (i.e., lower-peak magnitude) of the same pulse of the PPW signal $SM_2$, and an estimated mean BP value corresponding to the mean magnitude of the same pulse of the PPW signal $SM_2$. The mean magnitude of each pulse of the PPW signal $SM_2$ may be defined as the height or magnitude of the center of gravity of an area defined by the waveform of that pulse and a base line passing through the lower-peak point (i.e., minimum magnitude) of that pulse.

The selector valve 16 and the first air pump 18 cooperate with the control device 28 to provide a cuff-pressure regulating device 70 which regulates the pressure of the cuff 10 (i.e., cuff pressure), which is detected by the pressure sensor 14 when an oscillometric BP measurement using the cuff 10 is carried out by the standard-BP determining means 72. The cuff-pressure regulating device 70 changes the cuff pressure according to a well-known procedure, so that the standard-BP determining means 72 determines standard BP values of the patient using the cuff 10 just before the commencement of operation of the exercise-load control means 84 and so that the relationship determining means 74 updates the MBP-$P_M$ relationship based on the standard BP values newly measured using the cuff 10. For example, the regulating device 70 increases the cuff pressure up to a target value, e.g., 180 mmHg, which is higher than an estimated systolic BP value of the patient and subsequently decreases the cuff pressure slowly at the rate of 2 to 3 mmHg/sec during a measurement period in which standard BP values of the patient are determined by the standard-BP determining means 72 according to a well-known oscillometric BP determining algorithm. After the standard-BP measuring operation, the regulating device 70 quickly deflates the cuff 10 down to the atmospheric pressure.

In the present embodiment, the cuff-pressure regulating means 70, the standard-BP determining means 72, the PPW sensor 38, the flat-surface-pressing-force changing device 54, the relationship determining means 74, and the BP estimating means 76 cooperate with one another to provide a blood-pressure measuring device 78 which successively and non-invasively measures a blood pressure MBP of the patient in synchronism with the heartbeat of the patient.

The control device 28 also functions as a pulse-rate (PR) determining means 80 which successively measures a pulse rate, PR, of the patient in synchronism with the heartbeat of the patient. For example, the PR determining means 80 determines a pulse rate PR from the time difference between each pair of successive heartbeat-synchronous pulses of the PPW signal $SM_2$ supplied from the PPW sensor 38.

The control device 28 also functions as a PRP calculating means 82 which successively calculates a product, PRP, of a pulse rate PR and a blood pressure MBP (PRP=PR×MBP) in synchronism with the heartbeat of the patient.

The exercise-load control means 84 controls the exercise-load changing device (brake) 68 to change the exercise load applied to the patient by the exercise-load applying device (ergometer) 6, so that the pressure-rate products PRP successively calculated by the PRP calculating means 82 substantially coincide with the predetermined target value $PRP_M$ input by the operator through the input device 60.

Under control of the control means 84, the changing device 68 changes the exercise load by changing the resistance applied to the rotation of the rotary plate 67 which is rotated by the patient through the pedals 65 and the chain 66.

The control device 28 also functions as an abnormality identifying means 86 which identifies an abnormality of the patient when a pulse rate PR determined by the PR determining means 80 is greater than a reference value, $PR_r$. When the identifying means 86 identifies the abnormality, the control means 84 controls the exercise-load changing device 68 to decrease, to zero, the exercise load applied to the patient by the exercise-load applying device 6, i.e., the braking force or resistance applied to the rotary member 67 which is rotated with the pedals 65. The identification of this abnormality is indicated on the display device 36.

Figure 5:
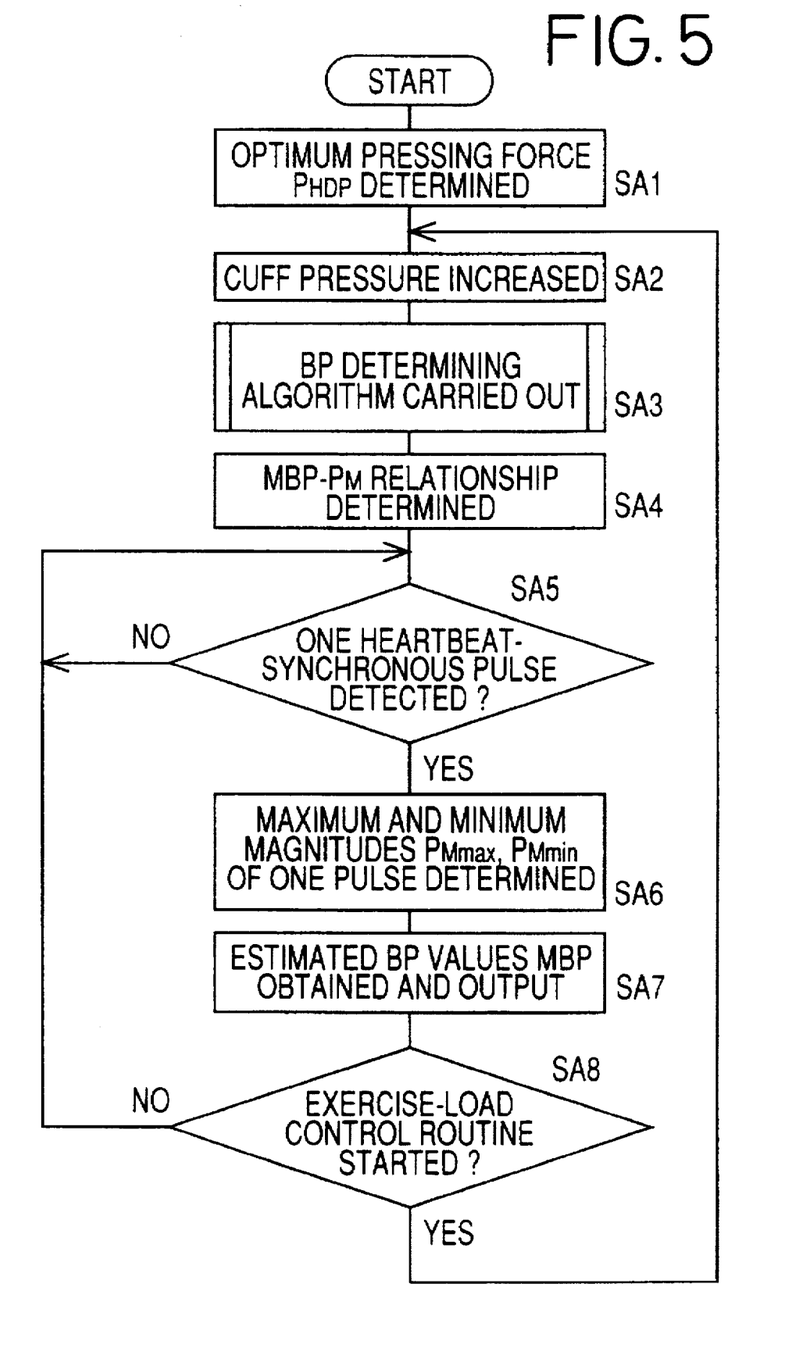
FIG. 5 is a flow chart representing a blood-pressure-measurement control routine according to which the control device of the apparatus of FIG. 1 operates for successively determining a blood pressure of a person in synchronism with the heartbeat of the person.
Figure 6:
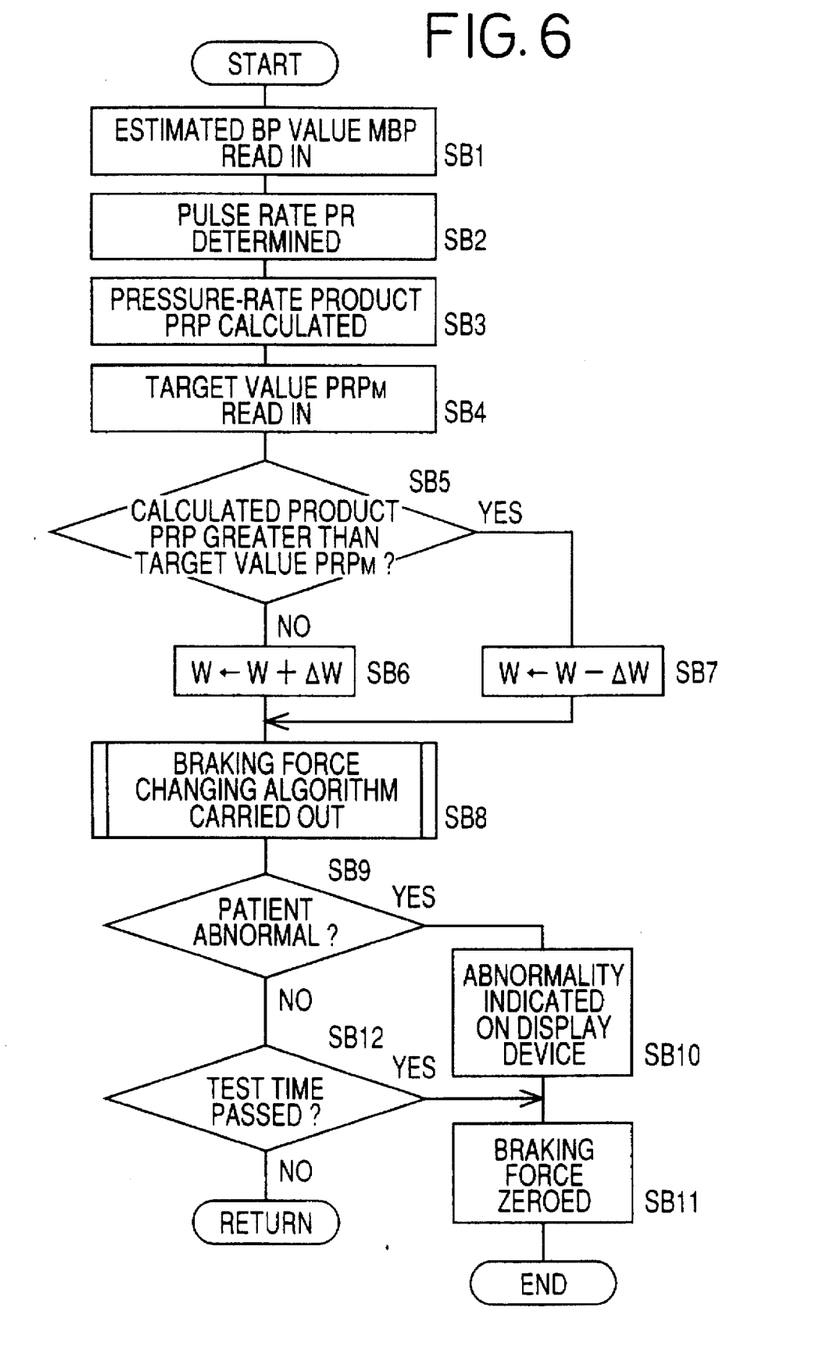
FIG. 6 is a flow chart representing an exercise-load control routine according to which the control device of the apparatus of FIG. 1 operates for changing the exercise load applied to the person by an ergometer as an exercise-load applying device of the apparatus.

Next, there will be described the operation of the exercise apparatus 4 constructed as described above, by reference to the flow charts of FIGS. 5 and 6 representing the control programs pre-stored in the ROM 32. More specifically, the flow chart of FIG. 5 represents a successive BP measurement routine in which an estimated BP value MBP is obtained from each of heartbeat-synchronous pulses of the PPW signal $SM_2$, and the flow chart of FIG. 6 represents an exercise-load control routine in which the exercise load applied to a patient by the ergometer 6 is controlled so that the pressure-rate products PRP substantially coincide with the target value $PRP_M$.

First, at Step SA1, the CPU 30 of the control device 28 controls the second air pump 56 and the pressure regulator valve 58 to increase slowly the pressure of the pressure chamber 45, and determines, as an optimum pressing force $P_{HDP}$, a pressure of the chamber 45 when the PPW sensor 38 detects a maximum pulse having the greatest amplitude of the respective amplitudes of all the pulses detected thereby during the slow increasing of the pressure of the chamber 45. Subsequently, the CPU 30 holds the pressure of the chamber 45 at the thus determined optimum pressing force $P_{HDP}$. Thus, the optimum pressing force $P_{HDP}$ is applied to the PPW sensor 38 to flatten partially the wall of the radial artery 48 via the body surface 40.

Next, the control of the CPU 30 proceeds with Step SA2 to start increasing the pressure of the cuff 10 for measuring standard BP values of the patient. Step SA2 corresponds to the cuff-pressure regulating means 70. Step SA2 is followed by Step SA3 to carry out a known oscillometric BP determining algorithm. More specifically described, the selector valve 16 is switched to the first state and the first air pump 18 is operated, so that the cuff pressure continues to increase up to a target pressure (e.g., 180 mmHg) higher than an estimated systolic BP value of the patient. Subsequently, the air pump 18 is stopped and the selector valve 16 is switched to the second state, so that the cuff pressure decreases at a predetermined low rate (e.g., about 3 mmHg/sec). Based on the variation of respective amplitudes of heartbeat-synchronous pulses of the cuff-pulse-wave (CPW) signal $SM_1$ obtained during this slow decreasing of the cuff pressure, the CPU 30 determines a systolic, a mean, and a diastolic BP value $BP_{SYS}$, $BP_{MEAN}$, $BP_{DIA}$ of the patient according to the oscillometric BP determining algorithm. More specifically, the CPU 30 determines, as the systolic BP value $BP_{SYS}$, a cuff pressure at the time when the pulse amplitudes significantly largely increase, determines, as the diastolic BP value $BP_{DIA}$, a cuff pressure at the time when the pulse amplitudes significantly largely decrease, and determines, as the mean BP value $BP_{MEAN}$, a cuff pressure at the time when the pulse amplitudes become maximum. In addition, the CPU 30 determines a pulse rate PR of the patient based on the time difference or interval between respective upper peaks of two successive heartbeat-synchronous pulses of the CPW signal $SM_1$. The thus measured standard BP values and pulse rate PR are stored in the RAM 34 and displayed on the display device 36. Then, the selector valve 16 is switched to the third state, so that the cuff pressure is quickly decreased to the atmospheric pressure. Step SA3 corresponds to the standard-BP determining means 72.

Subsequently, the control of the CPU 30 goes to Step SA4 to determine a relationship between estimated BP value MBP and magnitude $P_M$ of pressure pulse wave (i.e., voltage of the pressure-pulse-wave (PPW) signal $SM_2$) as shown in FIG. 4. More specifically described, the CPU 30 newly reads in one heartbeat-synchronous pulse of the PPW signal $SM_2$ supplied from the PPW sensor 38, determines a maximum and a minimum magnitude $P_{Mmax}$, $P_{Mmin}$ of the one pulse, and determines the previously-indicated linear function (1) based on the systolic and diastolic BP values $BP_{SYS}$, $BP_{DIA}$ of the patient measured at Step SA3 and the thus determined maximum and minimum magnitudes $P_{Mmax}$, $P_{Mmin}$ of the one pulse of the PPW signal $SM_2$. Step SA4 corresponds to the relationship determining means 74.

After the MBP-$P_M$ relationship shown in FIG. 4 is determined at Step SA4, the control of the CPU 30 goes to Step S5 to judge whether the CPU 30 has read in one heartbeat-synchronous pulse of the PPW signal $SM_2$ supplied from the PPW sensor 38 being pressed at the optimum pressing force $P_{HDP}$. If a negative judgment is made at Step SA5, the CPU 30 waits for detecting one pulse of the PPW signal $SM_2$. Meanwhile, if a positive judgment is made at Step SA5, the control of the CPU 30 goes to Step SA6 to determine a maximum (upper-peak) magnitude $P_{Mmax}$ and a minimum (lower-peak) magnitude $P_{Mmin}$ of the one pulse of the PPW signal $SM_2$. Step SA6 is followed by Step SA7 to estimate a systolic and a diastolic BP value $MBP_{SYS}$, $MBP_{DIA}$ (i.e., estimated BP values) of the patient, based on the maximum and minimum magnitudes $P_{Mmax}$, $P_{Mmin}$ of the one pulse of the PPW signal $SM_2$ determined at Step SA6, according to the MBP-$P_M$ relationship determined at Step SA4. The CPU 30 controls the display device 36 to display, on its image screen, not only the estimated BP values MBP but also the waveform of the one pulse that is continuous with the waveforms of the previous pulses. Steps SA6 and SA7 correspond to the BP estimating means 76.

Subsequently, the control of the CPU 30 goes to Step SA8 to judge whether the exercise-load control routine of FIG. 6 should be started. When an exercise-load control start button (not shown) provided on a handle of the ergometer 6 is pushed by the patient, or when the rotation of the pedals 65 of the ergometer 6 is started by the patient, a positive judgment is made at Step SA8. If a negative judgment is made at Step SA8, the control of the CPU 30 goes back to Step SA5 and the following steps, i.e., BP monitor routine in which estimated systolic and diastolic BP values $MBP_{SYS}$, $MBP_{DIA}$ are obtained for each heartbeat-synchronous pulse of the PPW signal $SM_2$ and are displayed on the display device 36. On the other hand, if a positive judgment is made at Step SA8, the control goes back to Step SA2 and the following steps to update the MBP-$P_M$ relationship, i.e., determine a new MBP-$P_M$ relationship. That is, just before the control of the CPU 30 enters the exercise-load control routine of FIG. 6, new standard BP values are measured at Step SA3, and a new MBP-$P_M$ relationship is determined based on the new standard BP values at Step SA4.

While estimated systolic and diastolic BP values $MBP_{SYS}$, $MBP_{DIA}$ are obtained for each of successive heartbeat-synchronous pulses of the PPW signal $SM_2$, according to the newly determined or updated MBP-$P_M$ relationship, the control of the CPU 30 enters the exercise-load control routine of FIG. 6. First, at Step SB1, the CPU 30 reads in the estimated systolic BP value $MBP_{SYS}$ obtained for one heartbeat-synchronous pulse of the PPW signal $SM_2$. Step SB1 is followed by Step SB2 to determine an actual pulse rate PR of the patient in the previously-described manner. Step SB2 corresponds to the PR determining means 80. Subsequently, the control of the CPU 30 goes to Step SB3 to calculate a pressure-rate product PRP by multiplying the estimated systolic BP value $MBP_{SYS}$ by the actual pulse rate PR. Step SB3 corresponds to the PRP calculating means 82. Step SB3 is followed by Step SB4 to read in the target pressure-rate product $PRP_M$ from the input device 60. The input device 60 includes a memory which stores the target value $PRP_M$ input by the operator.

Subsequently, the control of the CPU 30 goes to Steps SB5 to SB8 to control the electromagnetic brake 68 so that the pressure-rate product PRP calculated at Step SB3 may substantially coincide with the target value $PRP_M$ read from the input device 60 at Step SB4. More specifically, at Step SB5, the CPU 30 judges whether the pressure-rate product PRP calculated at Step SB3 is greater than the target value $PRP_M$. If a negative judgment is made at Step SB5, the control of the CPU 30 goes to Step SB6 to increment the work efficiency or power, W, of the brake 68 by a predetermined positive value, $\Delta W$. On the other hand, if a positive judgment is made at Step SB5, the control of the CPU 30 goes to Step SB7 to decrement the power W of the brake 68 by the value $\Delta W$. The current power W of the brake 68 had been updated at Step SB6 or SB7 in the previous cycle in accordance with the exercise-load control routine of FIG. 6. Step SB6 or Step SB7 is followed by Step SB8 to adjust an exciting current supplied to an exciting coil of the electromagnetic brake 68, i.e., the braking torque of the brake 68, so that the brake 68 does the thus changed work W. Steps SB5 to SB8 correspond to the exercise-load control means 84.

Step SB8 is followed by Step SB9 to judge whether the patient who is doing exercise on the ergometer 6 is abnormal. For example, a positive judgment is made when the pulse rate PR determined at Step SB2 is greater than a reference value $PR_r$. The reference value $PR_r$ may be a pulse rate higher by 75 to 100% than the standard pulse rate PR measured at Step SA3 of FIG. 5. This percentage may be selected by the operator to fall in the range of 75 to 100% and input to the input device 60. Step SB9 corresponds to the abnormality identifying means 86. If a positive judgment is made at Step SB9, the control of the CPU 30 goes to Step S10 to control the display device 36 to indicate that the patient is abnormal, and then to Step SB11 to zero the work W of the brake 68, i.e., the resistance applied to the rotation of the rotary member 67 of the ergometer 6. On the other hand, if a negative judgment is made at Step SB9, the control of the CPU 30 goes to Step SB12 to judge whether a timer (not shown) of the microcomputer has counted up a predetermined time since the commencement of the current exercise-load control operation. This time is so predetermined as to be appropriate for the exercise test. If a negative judgment is made at Step SB12, the CPU 30 returns to Step SB1 and the following steps. On the other hand, if a positive judgment is made at Step SB12, the CPU 30 zeroes the work W of the brake 68, i.e., the resistance to the rotation of the rotary member 67 of the ergometer 6, thereby stopping applying the exercise load to the patient.

As is apparent from the foregoing description, the present exercise apparatus 4 successively calculates the pressure-rate product PRP as the product of the pulse rate PR and the estimated (systolic) BP value MBP ($MBP_{SYS}$). The pressure-rate product PRP appropriately indicates the load internally applied to the patient. Since the exercise-load control means 84 controls the exercise load applied to the patient by the ergometer 6, in such a manner that the current pressure-rate product PRP substantially coincides with the target value $PRP_M$, the exercise load applied to the patient is adjusted depending upon the current pulse rate PR and blood pressure MBP. Thus, the present apparatus 4 can apply a necessary and sufficient exercise load to any patient while simultaneously preventing an excessively high load from being applied to the patient who may be in bad shape or may have a low cardiac function, thereby avoiding the patient from suffering, e.g., heart attack. In addition, the BP measuring device 78 successively and non-invasively measures or estimates the BP values MBP in synchronism with the heartbeat of the patient, and accordingly the PRP calculating means 82 successively calculates the pressure-rate products PRP in synchronism with the heartbeat of the patient. Thus, the CPU 30 controls, without delay, the exercise load applied to the patient so that the current pressure-rate product PRP substantially coincides with the target value $PRP_M$. That is, the CPU 30 controls the brake 68 so that the ergometer 6 can continue to apply an appropriate exercise load to the patient.

In the illustrated embodiment, the BP measuring means 78 includes the cuff-pressure regulating means 70 which changes the pressing pressure of the cuff 10 applied to the brachial artery of the upper arm 12, at a predetermined rate; the standard-BP determining means 72 which determines a standard BP value of the patient based on the variation of the heartbeat-synchronous wave $SM_1$ obtained while the pressing force of the cuff 10 is changed; the PPW sensor 38 adapted to be pressed against the radial artery 48 of the patient via the skin tissue 40 above the artery 48 so as to detect a magnitude of the PPW $SM_2$ produced from the artery 48 in synchronism with the heartbeat of the patient; the relationship determining means 74 which determines a relationship between blood pressure and PPW magnitude, based on the standard BP value determined by the standard-BP determining means 72 and the magnitude of the PPW $SM_2$ detected by the PPW sensor 38; and the BP estimating means 76 which successively estimates a BP value of the patient, based on a magnitude of each of a plurality of heartbeat-synchronous pulses of the actual PPW $SM_2$ detected by the PPW sensor 38, according to the relationship determined by the relationship determining means 74. A standard BP value or values determined by the standard-BP determining means 72 are highly reliable, and a relationship between BP value and PPW magnitude is determined based on the highly reliable standard BP value or values and the magnitude or magnitudes of the PPW $SM_2$ detected by the PPW sensor 38. The BP estimating means 76 successively estimates a BP value MBP of the patient, based on a magnitude of each of heartbeat-synchronous pulses of the actual PPW $SM_2$ detected by the PPW sensor 38, according to the thus determined relationship between BP value and PPW magnitude. Thus, the estimated BP values MBP, successively obtained in synchronism with the heartbeat of the patient, enjoy a considerably high accuracy.

In the illustrated embodiment, the cuff 10 is used as a pressing device which presses a body portion of a person as a subject, and the cuff-pressure regulating means 70 is used as a cuff-pressure changing device which changes the air pressure in the cuff 10. The standard-BP determining means 72 determines a standard BP value or values of the person based on the variation of respective amplitudes of heartbeat-synchronous pulses of the CPW $SM_1$ that is a pressure oscillation produced in the cuff 10 while the cuff pressure is changed. This is a so-called oscillometric BP measuring method that has been proved to be highly reliable. Since an $MBP-P_M$ relationship is determined based on the thus determined standard BP value or values, the BP values MBP estimated according to the $MBP-P_M$ relationship enjoy a high reliability.

In the illustrated embodiment, the PPW sensor 38 includes the press member 50 having the flat surface 51 adapted to be pressed against the radial artery 48 of the patient via the skin tissue 40, and the pressure sensing elements (not shown) are arranged in an array in the flat surface 51. The flat-surface pressing device 44, 45, 46 presses the flat surface 51 against the radial artery 48 via the skin tissue 40, and the BP measuring means 78 includes the flat-surface-pressing-force changing device 54 which controls the flat-surface pressing device to press the flat surface 51 against the artery 48 via the skin 40 such that a portion of the wall of the artery 48 is flattened under the flat surface 51 and the skin 40. In this case, since a portion of the wall of the artery 48 is flattened under the flat surface 51 in which the pressure sensing elements are provided, the PPW detected by each of the pressure sensing elements is least influenced by the tensile force of the arterial wall. Thus, the PPW detected by the PPW sensor 38 enjoys a high accuracy and accordingly the BP-PPW relationship determined based on the detected PPW enjoys a high accuracy. In addition, the estimated BP values MBP and the calculated pressure-rate products PRP also enjoy a high accuracy. The PPW sensor 38 may be modified to be pressed against a dorsal pedal artery of an ankle of a leg of a person.

In the illustrated embodiment, the standard-BP determining means 72 determines one or more standard BP values of the patient, before the exercise-load control means 84 begins controlling the exercise-load changing device (electromagnetic brake) 68 to change the exercise load applied to the patient by the exercise-load applying device (ergometer) 6 so that the pressure-rate products PRP successively calculated by the PRP calculating means 82 substantially coincide with the predetermined target value $PRP_M$, and the relationship determining means 74 determines an $MBP-P_M$ relationship between BP value and PPW magnitude, based on the standard BP value or values determined by the standard-BP determining means 72 and the magnitude of the PPW $SM_2$ detected by the PPW sensor 38 before the control means 84 begins controlling the exercise-load changing device 68. In the case where the $MBP-P_M$ relationship is determined just before the commencement of the exercise-load control operation of the control means 84, BP values of the patient are estimated by the BP estimating means 76 with higher accuracy according to the new $MBP-P_M$ relationship and accordingly pressure-rate products PRP of the patient are calculated with higher accuracy.

The present exercise apparatus includes the abnormality identifying means 86 which identifies an abnormality of the patient by judging whether each of the pulse rates PR successively measured by the pulse-rate determining means 80 is greater than a reference value $PR_s$, and the exercise-load control means 84 controls, when the abnormality identifying means 86 identifies the abnormality that one of the pulse rates PR is found to be greater than the reference value $PR_s$, the exercise-load changing device 68 to zero the exercise load applied to the patient by the exercise-load applying device 6. Even when an abnormality occurs to the patient, the present exercise apparatus can effectively prevent an excessively high exercise load from being applied to the patient.

While the present invention has been described in its preferred embodiment, the present invention may otherwise be embodied.

Figure 7:
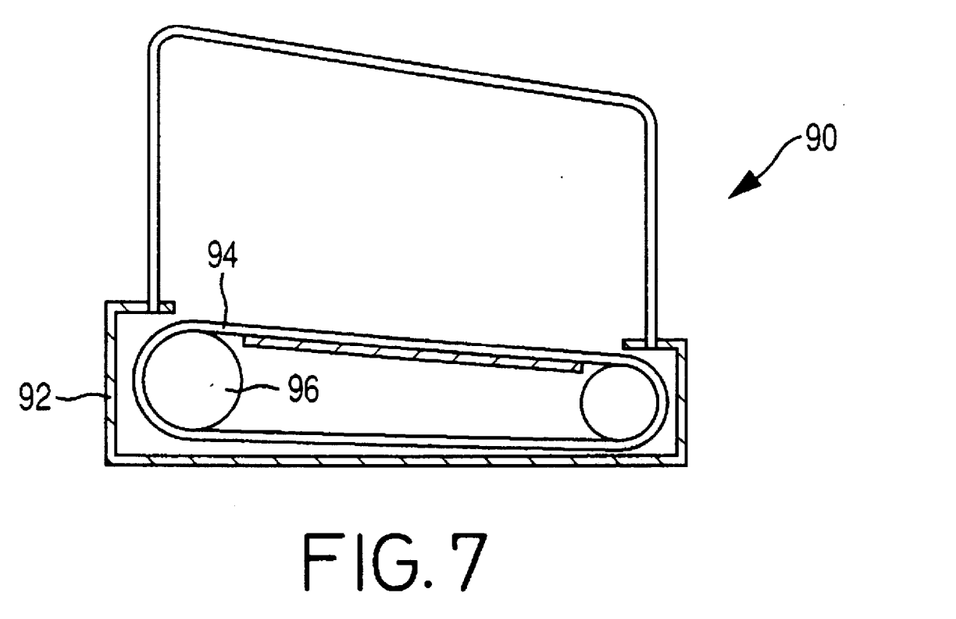
FIG. 7 is a view of a treadmill as an exercise-load applying device employed in another exercise apparatus as a second embodiment of the present invention.

For example, although in the illustrated embodiment the ergometer 6 is employed as the exercise-load applying device, the ergometer 6 may be replaced by a treadmill 90 as shown in FIG. 7. The treadmill 90 includes a base member 92 which supports an endless belt 94 such that the belt 94 is moved or circulated by an electric motor 96 while a patient walks or runs on the moving belt 94. In this case, the control device 28 supplies a command single to the electric motor 96 so that the motor 96 changes the speed of movement or circulation of the belt 94, thereby changing the exercise load applied to the patient. Thus, the electric motor 96 functions as the exercise-load changing device, like the electromagnetic brake 68.

In the illustrated embodiment, the control device 28 functions as the PR determining means 80 which determines the PR values of the patient from the difference between the respective times of occurrence of each pair of successive heartbeat-synchronous pulses of the PPW signal $SM_2$ supplied from the PPW sensor 38. However, the PPW signal $SM_2$ may be replaced by a photoelectric pulse wave signal produced by a blood-oxygen-saturation sensor as one of photoelectric pulse wave sensors, or an impedance pulse wave signal produced by an impedance pulse wave sensor.

The BP measuring device 8 or the BP measuring means 78 may be replaced by a different device which includes a volumetric pulse wave sensor, as one of photoelectric pulse wave sensors, which detects a volumetric pulse wave from a person; means for determining a relationship between (a) blood pressure and (b) area defined by a heartbeat-synchronous pulse of volumetric pulse wave; and means for estimating a BP value of the person based on the area defined by each of successive heartbeat-synchronous pulses of the volumetric pulse wave detected by the sensor according to the determined relationship.

While in the illustrated embodiment the BP measuring means 78 measures BP values MBP of a patient for each of heartbeat-synchronous pulses of the PPW signal $SM_2$, the BP measuring means 78 may be modified to measure one or more BP values MBP of a patient for every second, third, fourth, . . . heartbeat-synchronous pulse of the PPW signal $SM_2$.

Although in the illustrated embodiment the relationship determining means 74 determines, as the MBP-$P_M$ relationship, the linear function defined by the expression (1), the relationship determining means 74 may be modified to determine, as the MBP-$P_M$ relationship, a quadratic or higher-order function which may include, if necessary, a correction term.

Although in the illustrated embodiment the standard-BP determining means 72 determines one or more standard BP values of the patient based on the variation of the CPW $SM_1$ obtained while the cuff pressure $P_c$ is slowly decreased, the standard-BP determining means 72 may be modified to determine one or more standard BP values of a person based on the variation of the CPW $SM_1$ obtained while the cuff pressure $P_c$ is slowly increased.

While in the illustrated embodiment the standard-BP determining means 72 determines one or more standard BP values of the patient according to a known oscillometric method, the standard-BP determining means 72 may be replaced by a different BP measuring device which also includes a cuff and a device for chaining the cuff pressure and which determines, according to a known Korotkoff method, one or more standard BP values of a person based on a cuff pressure at the time when a Korotkoff sound is first detected, and/or last detected, from person's body portion (e.g., upper arm) being pressed under the cuff while the cuff pressure is changed by the cuff-pressure changing device.

Although in the illustrated embodiment the abnormality identifying means 86 identifies an abnormality of the patient based on the pulse rates PR successively determined by the PR determining means 80, the abnormality identifying means 86 may be replaced by a different abnormality identifying device which identifies an abnormality of a person based on the pressure-rate products PRP successively determined by the PRP calculating means 82. In the latter case, the abnormality identifying device may identify an abnormality of a person when one of the pressure-rate products PRP is greater than a reference value, $PRP_r$, which is significantly higher than the target value $PRP_M$. The reference value $PRP_r$ may be input through the input device 60.

While in the illustrated embodiment the relationship determining means 74 determines the MBP-$P_M$ relationship just after the operation of the present exercise apparatus is started and just before the operation of the exercise-load control means 84 is started, the relationship determining means 74 may be modified to update the MBP-$P_M$ relationship at a predetermined cyclic period, e.g., from 5 to 30 minutes. In the latter case, the cyclic period may be input through the input device 60.

It is to be understood that the present invention may be embodied with other changes, improvements, and modifications that may occur to those skilled in the art without departing from the spirit and scope of the invention defined in the appended claims.

What is claimed is:

1. An exercise apparatus comprising:
   an exercise-load applying device which applies an exercise load to a person;
   an exercise-load changing device which changes the exercise load applied to the person by said exercise-load applying device;
   a pulse-rate measuring device which successively measures a pulse rate of the person in synchronism with a heartbeat of the person;
   a blood-pressure measuring device which successively and non-invasively measures a blood pressure of the person in synchronism with the heartbeat of the person;
   a calculating device which successively calculates a product of said pulse rate and said blood pressure in synchronism with the heartbeat of the person; and
   a control device which controls said exercise-load changing device to change the exercise load applied to the person by said exercise-load applying device, so that the products successively calculated by said calculating device substantially coincide with a predetermined target value.

2. An exercise apparatus according to claim 1, wherein said blood-pressure measuring device comprises:
   a pressing device which provides a pressing force to press a body portion of the person;
   a pressing-force changing device which changes the pressing force of said pressing device;
   standard-blood-pressure determining means for determining a standard blood pressure of the person based on a heartbeat-synchronous wave obtained while the pressing force of said pressing device is changed by said pressing-force changing device;
   a pressure-pulse-wave sensor adapted to be pressed against an artery of the person via a skin tissue above the artery so as to detect a magnitude of a pressure pulse wave produced from the artery in synchronism with the heartbeat of the person;

relationship determining means for determining a relationship between blood pressure and magnitude of pressure pulse wave, based on the standard blood pressure determined by said standard-blood-pressure determining means and the magnitude of the pressure pulse wave detected by said pressure pulse wave sensor; and blood-pressure estimating means for successively estimating a blood pressure of the person, based on a magnitude of each of a plurality of heartbeat-synchronous pulses of the pressure pulse wave detected by said pressure pulse wave sensor, according to the relationship determined by said relationship determining means.

3. An exercise apparatus according to claim 2, wherein said pressing device comprises an inflatable cuff adapted to be wound around the body portion of the person, said pressing-force changing device comprising a cuff-pressure changing device which changes a fluid pressure in said cuff, said standard-blood-pressure determining means comprising means for determining the standard blood pressure of the person based on a variation of respective amplitudes of a plurality of heartbeat-synchronous pulses of the heartbeat-synchronous wave which is a pressure oscillation produced in said cuff while the pressure of the cuff is changed by said cuff-pressure changing device.

4. An exercise apparatus according to claim 2, wherein said pressing device comprises an inflatable cuff adapted to be wound around the body portion of the person, said pressing-force changing device comprising a cuff-pressure changing device which changes a fluid pressure in said cuff, said standard-blood-pressure determining means comprising means for determining the standard blood pressure of the person based on a fluid pressure of said cuff at a time when a Korotkoff sound is first detected, or last detected, from the body portion while the pressure of the cuff is changed by said cuff-pressure changing device.

5. An exercise apparatus according to claim 2, wherein said pressure pulse wave sensor comprises a flat surface adapted to be pressed against the artery of the person via the skin tissue, a plurality of pressure sensing elements arranged in the flat surface, and a flat-surface pressing device which presses the flat surface against the artery via the skin tissue, and wherein said blood-pressure measuring device comprises means for controlling the flat-surface pressing device to press the flat surface against the artery via the skin tissue such that a portion of a wall of the artery is flattened under the flat surface.

6. An exercise apparatus according to claim 2, wherein said standard-blood-pressure determining means comprises means for determining the standard blood pressure of the person, before said control device begins controlling said exercise-load changing device to change the exercise load applied to the person by said exercise-load applying device so that the products successively calculated by said calculating device substantially coincide with the predetermined target value, and wherein said relationship determining means comprises means for determining the relationship between blood pressure and magnitude of pressure pulse wave, based on the standard blood pressure determined by the standard-blood-pressure determining means and the magnitude of the pressure pulse wave detected by said pressure pulse wave sensor before said control device begins controlling said exercise-load changing device.

7. An exercise apparatus according to claim 1, further comprising abnormality identifying means for identifying an abnormality of the person when one of the pulse rates successively measured by said pulse-rate measuring device is greater than a reference value, wherein said control device controls, when said abnormality identifying means identifies said abnormality, said exercise-load changing device to decrease the exercise load applied to the person by said exercise-load applying device.

8. An exercise apparatus according to claim 1, wherein said exercise-load applying device comprises a pair of pedals adapted to be rotated by a pair of feet of the person, respectively, and a rotary member which is rotatable with said pedals, and wherein said exercise-load changing device comprises means for changing a resistance to the rotation of said rotary member with said pedals.

9. An exercise apparatus according to claim 1, wherein said exercise-load applying device comprises an endless belt which is movable while supporting the person who is moving thereon, and wherein said exercise-load changing device comprises means for changing a speed of movement of said endless belt.

* * * * *